(12) United States Patent
Saeed et al.

(10) Patent No.: US 12,251,525 B2
(45) Date of Patent: Mar. 18, 2025

(54) INTERVENTIONAL DEVICE WITH ADJUSTABLE CONFIGURATION

(71) Applicant: Children's Medical Center Corporation, Boston, MA (US)

(72) Inventors: Mossab Y. Saeed, Revere, MA (US); Pedro J. Del Nido, Lexington, MA (US); Nikolay V. Vasilyev, Newton, MA (US); Niv Ad, North Bethesda, MD (US); Christopher J. Payne, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 57 days.

(21) Appl. No.: 16/762,076

(22) PCT Filed: Nov. 7, 2018

(86) PCT No.: PCT/US2018/059547
§ 371 (c)(1),
(2) Date: May 6, 2020

(87) PCT Pub. No.: WO2019/094413
PCT Pub. Date: May 16, 2019

(65) Prior Publication Data
US 2020/0337524 A1     Oct. 29, 2020

Related U.S. Application Data

(60) Provisional application No. 62/582,559, filed on Nov. 7, 2017.

(51) Int. Cl.
*A61B 1/00* (2006.01)
*A61B 1/005* (2006.01)
(Continued)

(52) U.S. Cl.
CPC ... *A61M 25/0141* (2013.01); *A61B 1/000094* (2022.02); *A61B 1/00082* (2013.01);
(Continued)

(58) Field of Classification Search
CPC ............ A61B 1/00009; A61B 1/00071; A61B 1/00082; A61B 1/00087; A61B 1/00094;
(Continued)

(56) References Cited

U.S. PATENT DOCUMENTS 5,379,765 A * 1/1995 Kajiwara ............. A61B 5/6853
607/122
5,645,519 A 7/1997 Lee et al.
(Continued)

FOREIGN PATENT DOCUMENTS

| EP | 0545739 | 6/1993 |
|---|---|---|
| WO | WO 2014/197625 | 12/2014 |
| WO | WO 2016/205694 | 12/2016 |

OTHER PUBLICATIONS

EP Extended European Search Report in European Appln. No. 18876332.0, dated Nov. 11, 2020, 8 pages.
(Continued)

*Primary Examiner* — Timothy J Neal
(74) *Attorney, Agent, or Firm* — Fish & Richardson P.C.

(57) ABSTRACT

A device for performing intervention procedures includes an elongated body having a first end and a second end. The elongated body includes a hollow tool channel extending through the elongated body from the first end to the second end. The tool channel is configured to receive an intervention tool and a length-adjusting element disposed at the first end or the second end of the elongated body. The length-adjusting element is configured to enable a length of the elongated body to be adjusted. The elongated body includes an angle-adjusting element disposed along the length of the
(Continued)

elongated body. The angle-adjusting element is configured to enable the elongated body to be bent. The device includes an imaging system disposed at the first end or the second end of the elongated body. The imaging system includes an imaging device and an illumination device.

17 Claims, 12 Drawing Sheets

(51) Int. Cl.
| | |
|---|---|
| A61B 1/06 | (2006.01) |
| A61B 1/07 | (2006.01) |
| A61B 5/318 | (2021.01) |
| A61M 25/01 | (2006.01) |

(52) U.S. Cl.
CPC ...... *A61B 1/00087* (2013.01); *A61B 1/00094* (2013.01); *A61B 1/00097* (2022.02); *A61B 1/0051* (2013.01); *A61B 1/0684* (2013.01); *A61B 1/07* (2013.01); *A61B 5/318* (2021.01); *A61B 2505/05* (2013.01); *A61B 2562/0271* (2013.01); *A61B 2576/023* (2013.01)

(58) Field of Classification Search
CPC ..... A61B 1/00097; A61B 1/0051; A61B 1/05; A61B 1/0676; A61B 1/0684; A61B 1/07; A61B 2505/05; A61B 2562/0271; A61B 2576/023; A61B 5/318; A61B 5/6853; A61M 2025/0046; A61M 2025/0161; A61M 2025/1086; A61M 25/0141; A61M 25/0158

See application file for complete search history.

(56) References Cited

U.S. PATENT DOCUMENTS

| | | | | |
|---|---|---|---|---|
| 5,865,801 | A * | 2/1999 | Houser | ............... A61B 5/036 607/101 |
| 8,758,229 | B2 | 6/2014 | Saadat et al. | |
| 2004/0082859 | A1 | 4/2004 | Schaer | |
| 2004/0102804 | A1 | 5/2004 | Chin | |
| 2005/0124856 | A1 * | 6/2005 | Fujikura | ........... A61M 25/0662 600/156 |
| 2007/0073269 | A1 * | 3/2007 | Becker | .................. A61M 25/10 604/509 |
| 2007/0135803 | A1 * | 6/2007 | Belson | ............... A61B 1/00154 606/1 |
| 2008/0183080 | A1 * | 7/2008 | Abraham | ............. A61B 1/3137 600/466 |
| 2008/0306442 | A1 * | 12/2008 | Bardsley | ............ A61B 17/3439 604/164.04 |
| 2009/0036744 | A1 | 2/2009 | Vayser | |
| 2009/0187098 | A1 * | 7/2009 | Makower | ............... A61B 90/36 600/101 |
| 2009/0299401 | A1 * | 12/2009 | Tilson | ............... A61M 25/1029 606/192 |
| 2010/0298832 | A1 * | 11/2010 | Lau | .................... A61B 17/8819 606/86 R |
| 2011/0130648 | A1 * | 6/2011 | Beeckler | ........... A61M 25/0054 600/424 |
| 2012/0232342 | A1 * | 9/2012 | Reydel | ..................... A61B 1/31 600/116 |
| 2013/0150693 | A1 * | 6/2013 | D'Angelo | ................ A61B 6/12 601/3 |
| 2015/0150442 | A1 | 6/2015 | Bashir et al. | |
| 2016/0278626 | A1 * | 9/2016 | Cornhill | ............ A61B 1/00082 |
| 2016/0367120 | A1 * | 12/2016 | Dupont | .................. A61B 1/015 |
| 2017/0086653 | A1 | 3/2017 | Yeung et al. | |
| 2018/0070800 | A1 * | 3/2018 | Yeung | ................ A61B 1/00087 |
| 2018/0344202 | A1 * | 12/2018 | Bar-Tal | ................. A61B 5/287 |
| 2019/0117044 | A1 * | 4/2019 | Anderson | ............. A61B 1/051 |
| 2020/0275968 | A1 * | 9/2020 | McGregor | ............ A61M 25/09 |

OTHER PUBLICATIONS

PCT International Preliminary Report on Patentability in International Appln. No. PCT/US2018/059547, dated May 12, 2020, 7 pages.

PCT International Search Report and Written Opinion in International Appln. No. PCT/US2018/059547, 12 pages.

EP Office Action in European Appln. No. 18876332.0, mailed on Apr. 3, 2023, 6 pages.

* cited by examiner

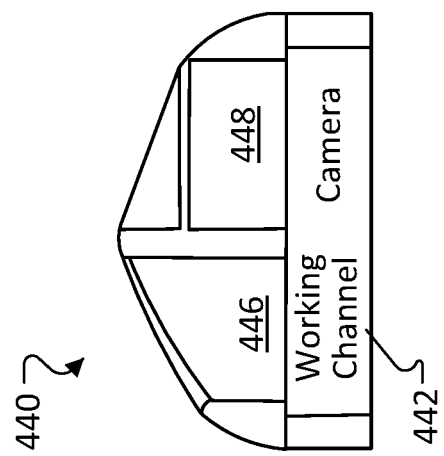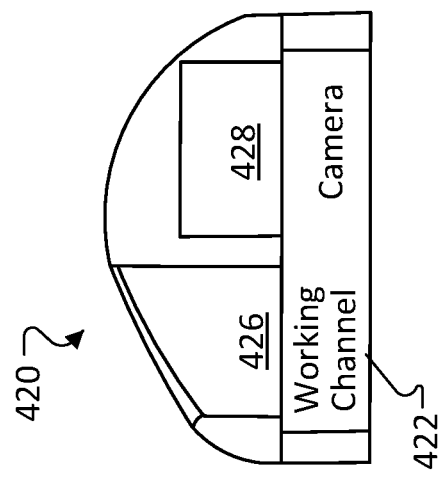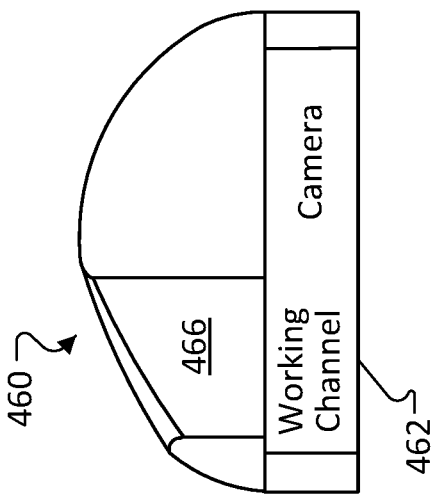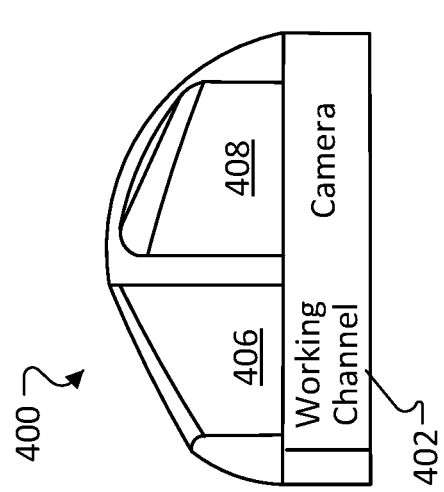

INTERVENTIONAL DEVICE WITH ADJUSTABLE CONFIGURATION

CLAIM OF PRIORITY

This application is a U.S. National Stage entry of International Application No. PCT/US2018/059547, filed on Nov. 7, 2018, which claims priority to U.S. Patent Application Ser. No. 62/582,559, filed on Nov. 7, 2017, the entire contents of both of which are incorporated here by reference.

BACKGROUND

Ventricular and supraventricular cardiac arrhythmias are common problems that can lead to serious health events, such as stroke or heart failure in atrial fibrillation or sudden cardiac death in ventricular tachycardia. Both conditions are often treated by cardiac ablation in which a barrier is created between the foci of the arrhythmia and the rest of the heart. In catheter-based cardiac ablation, a catheter is threaded through the femoral artery, through an upper extremity of a patient into the interior of the heart, or through the lower sternum edge (when approaching the exterior of the heart in conditions like ventricular arrhythmia). The catheter is used to ablate the appropriate region of the heart through any of a variety of approaches, e.g., by radiofrequency ablation, cryoablation, ultrasound ablation, or laser ablation. In surgical treatments for atrial fibrillation, such as the Cox-maze procedure, heart tissue is cut to create a barrier between the atrial fibrillation foci and the rest of the heart. In ventricular arrhythmia-like in ventricular tachycardia-surgical intervention is utilized to remove part of the ventricular tissues where the foci are located, or to create a barrier by ablating the area around the foci, approaching from the epicardial surface of the ventricle.

SUMMARY

This disclosure is based, at least in part, on the discovery that surgical procedures, such as minimally invasive beating heart extracardiac procedures, can be performed using instruments that provide tool delivery and imaging capabilities. The instruments described here have adjustable configurations to enable the instruments to be used with a wide variety of patient anatomies and to enable access to intervention sites, e.g., medical sites, surgical sites, diagnostic sites, or other intervention sites, through a single incision. For instance, the instruments can be lengthened, shortened, or bent to desired configurations, enabling complex procedures to be performed through a single, small incision. Integrated imaging systems enable imaging at intervention sites before, during, and after procedures, thus enabling image-guided positioning of the instruments and real time image guided interventional procedures.

In an aspect, a device for performing intervention procedures includes an elongated body having a first end and a second end. The elongated body includes a hollow tool channel extending through the elongated body from the first end to the second end. The tool channel is configured to receive an intervention tool and a length-adjusting element disposed at the first end or the second end of the elongated body. The length-adjusting element is configured to enable a length of the elongated body to be adjusted. The elongated body includes an angle-adjusting element disposed along the length of the elongated body. The angle-adjusting element is configured to enable the elongated body to be bent. The device includes an imaging system disposed at the first end or the second end of the elongated body. The imaging system includes an imaging device and an illumination device.

Embodiments can include one or more of the following features.

The length-adjusting element includes a telescopic element connected to the proximal end of the elongated body.

The length-adjusting element enables the length of the elongated body to be adjusted by up to about 50 mm.

The length-adjusting element enables the length of the elongated body to be adjusted by up to about 100 mm.

The angle-adjusting element includes a hinge disposed along the length of the elongated body.

The angle-adjusting element enables the elongated body to be bent to an angle of up to 100° about an axis.

The angle-adjusting element is configured to enable the elongated body to be bent to an angle of up to 140° about an axis.

The second end of the elongated body is flexible, the second end of the elongated body comprises a portion formed of a flexible material or having a flexible design.

The distal end of the body is configured to flex to an angle of up to 90°.

The imaging device includes one or more of a camera and an optical fiber.

The illumination device includes one or more of a light emitting diode (LED) or an optical fiber.

The device includes a transparent optical window attached to the distal end of the elongated body. The transparent optical window includes a tool channel extending therethrough and aligned with the tool channel in the elongate body. The transparent optical window includes an optical channel positioned in a field of view of the imaging device. The optical channel is filled with a fluid. The fluid has an index of refraction that is selected to obtain a target refraction of light between the illumination device and an intervention site. The fluid includes glycerol.

The device where the transparent optical window comprises a geometric shape positioned in a field of view of the imaging device to change a direction of the field of view.

The device includes an inflatable structure disposed along the elongated body. The inflatable structure has a surface roughness that differs from a surface roughness of an outer surface of the elongated body. The inflatable structure comprises a textured surface. The device includes a monitoring device integrated into the inflatable structure. The monitoring device includes one or more of an electrocardiogram (EKG), a temperature sensor, or infrared sensor. The inflatable structure is disposed toward the distal end of the elongated body. The position of the inflatable structure along the elongated body is adjustable. The device includes multiple or compartmented inflatable structures disposed along the elongated body.

The device includes a suction system configured to apply a suction at one or more of the distal end and a side of the elongated body.

The device includes a cautery mechanism disposed at the distal end of the elongated body.

The device includes a control mechanism mechanically connected to the length-adjusting element and the angle-adjusting element. The control mechanism is disposed at the proximal end of the elongated body. The control mechanism includes a first gear for controlling the length adjusting element and a second gear for controlling the angle adjusting element.

The first end is a proximal end of the elongated body, and the second end is a distal end of the elongated body. The length-adjusting element is disposed at the proximal end of the elongated body, and the imaging system is disposed at the distal end of the elongated body The length-adjusting element is disposed at the first end of the elongated body, and the imaging system is disposed at the second end of the elongated body.

In an aspect, a method for performing an intervention procedure at a target site in a patient includes inserting a device into the patient, wherein the device includes an elongated body including a tool channel extending therethrough from a proximal end to a distal end of the elongated body: adjusting one or more of a length and an angle of the elongated body to position the distal end of the elongated body at the target site; inserting an intervention tool through the tool channel; and obtaining an image of the target site, the intervention tool, or both using an imaging system disposed at the distal end of the elongated body of the device.

Embodiments can include one or more of the following features.

The method includes performing a cardiac intervention procedure in a beating heart.

The method includes performing a cardiac ablation procedure using the device.

Adjusting the length of the elongated body includes adjusting a telescopic element at the distal end of the elongated body.

Adjusting the angle of the elongated body includes adjusting a hinge disposed along the length of the elongated body.

The method includes inflating an inflatable structure disposed along the elongated body of the device. Inflating the inflatable structure includes filling the inflatable structure with fluid. Inflating of the inflatable structure stabilizes the device at the target site.

The method includes monitoring one or more of an electrocardiogram (EKG) and a temperature at the target site.

The method includes stabilizing the device with inflatable structures before inserting the intervention tool through the tool channel.

The adjustable configurations of the instruments described here enable the instruments to access intervention sites through a single incision, thus enabling minimally invasive procedures to be performed. For instance, the adjustable configuration of an instrument used in a cardiac ablation procedure can make the instrument easily maneuverable and stable at the ablation site, thus facilitating access to all areas of the heart through a single incision and enabling ablation to form a high quality, straight, and continuous barrier. The continuity of the ablated barrier that can be achieved through a single incision in a minimally invasive, beating heart procedure can result in higher success rates and longer lasting positive outcomes.

BRIEF DESCRIPTION OF DRAWINGS

FIGS. 4A-4D are cross-sectional views of embodiments of a transparent bulb of an adjustable configuration device.

DETAILED DESCRIPTION

Figure 1:
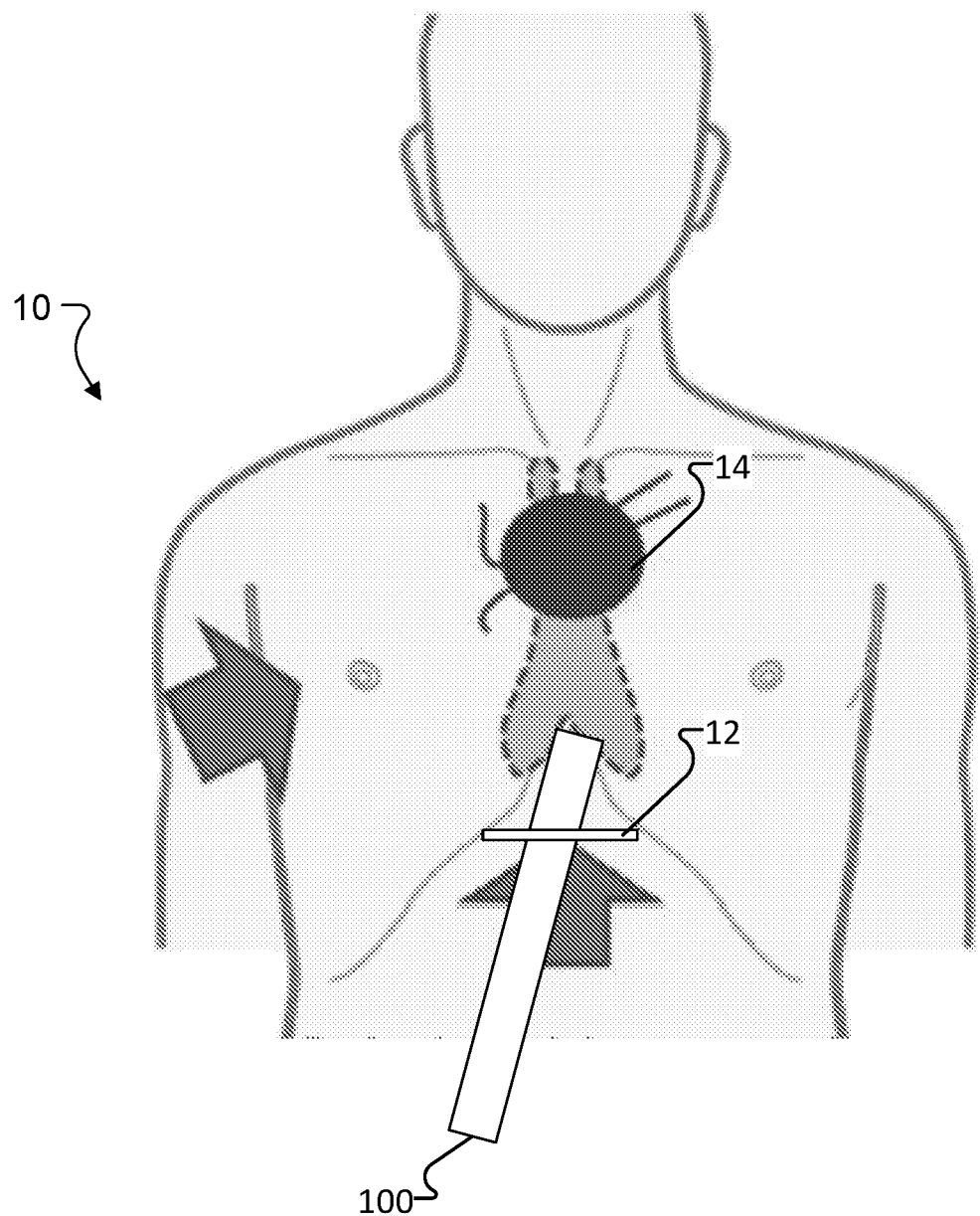
FIG. 1 is a diagram of a minimally invasive cardiac procedure.

Referring to FIG. 1, an adjustable intrapericardial navigation device 100 is used to introduce a cardiac ablation tool to treat atrial arrhythmia (e.g. atrial fibrillation) or ventricular arrhythmia (e.g. ventricular tachycardia) or any interventional tool in a patient 10. In a minimally invasive, beating heart cardiac ablation procedure, the device 100 is inserted into the patient through a single sub-xiphoidal incision 12 and advanced directly toward the patient's heart 14, e.g., through the pericardium and toward the epicardial surface of the ventricles or the atria of the heart 14. Device positioning and the intervention procedure can be performed under image guidance from an imaging system integrated at a distal end of the device.

Accessing the heart through a single sub-xiphoidal incision provides access to many areas in the heart 14 without putting other organs, such as abdominal organs (e.g. Liver) or lungs, at risk. To enable access to the heart from a sub-xiphoidal incision, the device 100 has an adjustable configuration. For instance, the length of the device 100 can be adjusted to reach from the incision to any intervention site in the heart or mediastinal space. In addition, the device 100 can be bent to achieve an angle appropriate for accessing the intervention site. Once the device 100 is positioned at the intervention site, the ability to further adjust the length of the device 100 and to bend the device 100 enables the device 100 to be moved smoothly in the vicinity of the intervention site, e.g., such that a straight and continuous area of cardiac tissue can be ablated. The device 100 can be inserted through a sub-xiphoidal (or any site of the chest) incision to reach the all areas of epicardial ventricular ablation on left and right ventricles (including, for instance, on the left ventricle: summit, basal-lateral, basal-inferior, mid-anterior, mid-lateral, mid-inferior and apex; on and on the right ventricle: anterior wall and inferior wall). The device 100 can be also used to approach sites on the left or right atrial surface of the heart, including around pulmonary veins or the superior or inferior vena cava, e.g., to ablate atrial arrhythmias. For instance, the device 100 can be positioned in the pericardial space and used to perform ablation for an appropriate period of time under direct vision by an imaging system integrated into the device 100.

Device Components

Figure 2A:
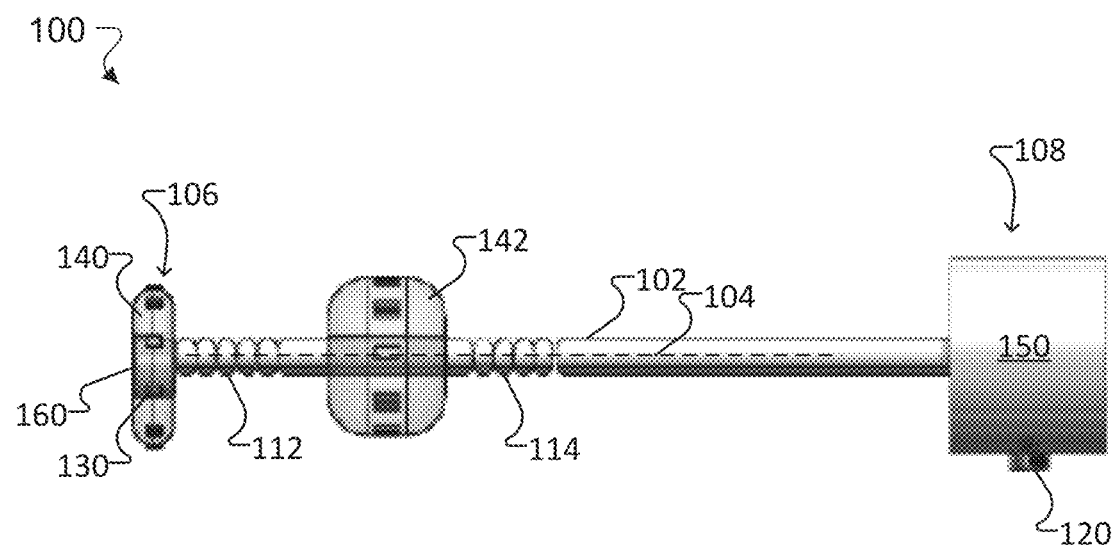
FIGS. 2A and 2B are diagrams of an adjustable configuration device.

Referring to FIG. 2A, the adjustable intrapericardial navigation device 100 includes an elongated, substantially cylindrical body 102. A tool channel 104 is formed through the length of the body 102, through which an interventional tool can be inserted to prepare for or perform the procedure. The tool can be a surgical tool for performing a surgical procedure. An imaging system 130 disposed at a distal end 106 of the device 100 enables direct visualization of the site of the surgical procedure, sometimes referred to as the surgical site.

The body 102 of the device can be formed from, or can include, a biocompatible material that is appropriate for use in surgical applications. For example, the body 102 can be formed from, or can include, a medical grade polymer plastic, such as polyvinylide fluoride, polypropylene, polyacetal, polycarbonate, Poly EtherEtherKetone (PEEK), or another polymer: silicone: silicone rubber, or another material. In some examples, the body 102 can be formed from a rigid or durable material, such as stainless steel, glass, PEEK, or another durable material, which can be sterilized for re-use. In some embodiments, the body 102 includes a combination of two or more of any of the foregoing materials. The body 102 can have a diameter of between about 10 mm and about 18 mm, e.g., about 10 mm, about 12 mm, about 14 mm, about 16 mm, about 18 mm, or another diameter. The length of the body can be between about 150 mm and about 250 mm, e.g., about 150 mm, about 200 mm, about 250 mm, or another length.

The tool channel 104 is sized to accept standard endoscopic surgical or interventional tools, such as a cautery tool, scissors, dissectors, graspers, a catheter, an insufflation needle, or another surgical, non-surgical, or interventional tool. A tool inserted into the tool channel 104 emerges from the tool channel 104 at the distal end 106 of the device 100 for access to the intervention site. The tool channel 104 can have a diameter of between about 2 mm and about 8 mm, e.g., about 2 mm, about 3.5 mm, about 5 mm, about 6 mm, about 8 mm, or another diameter. For instance, the tool channel 104 can be sized to receive the intervention tools expected to be used in conjunction with the device 100.

Figure 2B:
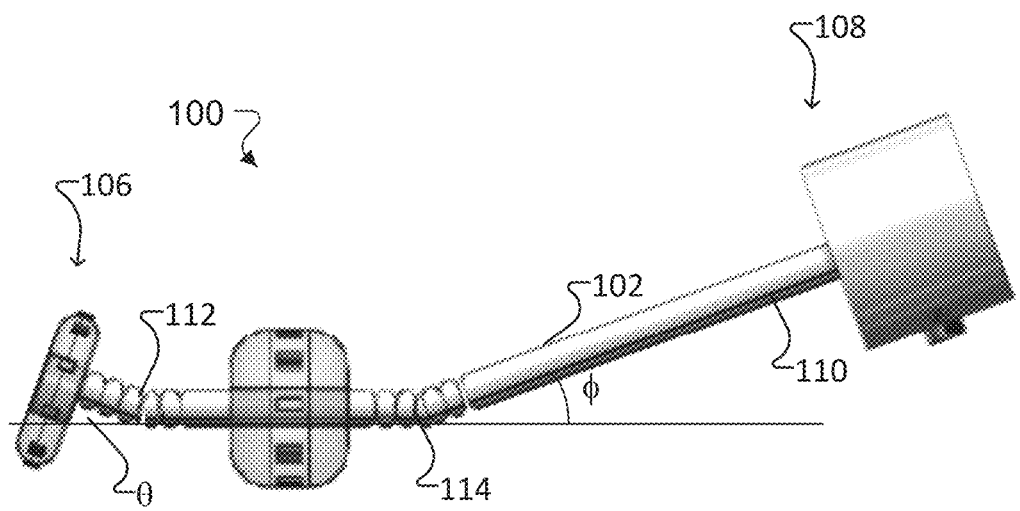

Referring now to both FIGS. 2A and 2B, the device 100 is configured to be generally usable with a variety of patient anatomies. As discussed in conjunction with FIG. 1, in the example of a cardiac ablation procedure, the device 100 is inserted into the body of the patient through a subxiphoidal incision and advanced toward the heart of the patient. The distance and relative angle between the subxiphoidal incision and the target area in the heart can vary among patients. The body 102 can be elongated or bent through the operation of an angle-adjustable element, a length-adjustable element, or combination of these features. For example, the body 102 can be elongated or bent through the operation of an extendible feature 110 or one or more bending features 112, 114, respectively, thus enabling the configuration of the device 100 to be adjusted to account for such variations in patient anatomy. The extendible feature can correspond to the length-adjustable element, and the one or more bending features 112, 114 can correspond to the angle-adjustable element. In addition, once the device 100 is positioned at the intervention site, the ability to adjust the length of the device 100 and to bend the device 100 can enable smooth movements of the distal end 106 of the device, e.g., so that a smooth and continuous area of tissue in the heart can be ablated.

Figure 3:
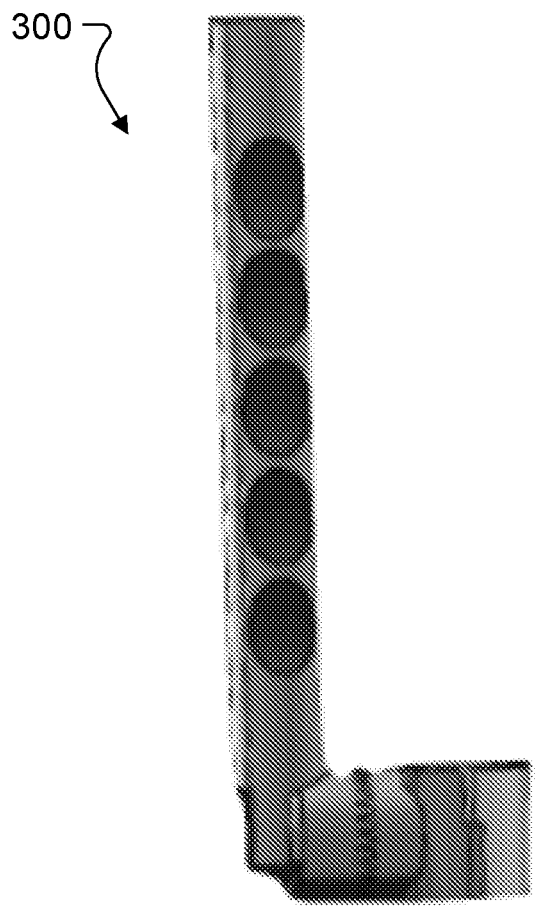
FIG. 3 is a diagram of a handle of an adjustable configuration device.

The extendible feature 110 is integrated into the body 102 at a proximal end 108 of the device 100 and enables the length of the device 100 to be adjusted, e.g., increased or decreased. For instance, the extendible feature 110 can be extended or retracted by up to about 40 mm, about 50 mm, about 60 mm, about 70 mm, about 80 mm, or another amount. The extendible feature 110 can be a telescoping feature, an accordion feature, or another type of extendible feature formed in the body 102 at the distal end 106 of the device. The extendible feature 110 can be controlled by a handle 300 (FIG. 3) at the proximal end 108 of the device, such as a grip that can be rotated to extend or retract the device 100.

A first bending feature 112 can be positioned at the distal end 106 of the device. The bending feature 112 can be a flexible tip of the body 102 that enables the angle of the tip to be adjusted on the vertical axis, the horizontal axis, or both, to an angle ▫ of up to 20 degrees, 30 degrees, 40 degrees, 50 degrees, or another amount relative to the axis of the unbent body 102. For instance, the bending feature 112 is flexible enough to spontaneously bend when pressure is applied to the bending feature 112, such as when the bending feature 112 is pressed against the heart. The bending feature 112 can be formed of a flexible, biocompatible polymer, such as silicone or another polymer. In some examples, the bending feature 112 can include a flexible design formed from any material (e.g. silicon, metal or plastic). The flexible design can include, for example, cut-outs or other geometric features that enable the bending feature 112 to bend.

A second bending feature 114 can be positioned along the length of the body 102 and enables the device 100 to be bent, thus adjusting an angle ▫ of the body 102. For instance, the bending feature 114 can enable the device 100 to be bent to an angle ▫ of up to 100 degrees, 120 degrees, 140 degrees, or another amount relative to the axis of the unbent body 102. The bending feature 114 can be a hinge, an accordion feature, a ball-and-socket joint, or another type of bending feature.

A control mechanism 120 disposed at a proximal end 108 of the device 100 enables a user, such as a surgeon or other interventionist, to control the operation of the device, such as to control the bending feature 112. In some examples, the control mechanism 120 can be mechanically coupled to the bending feature 112. For instance, the control mechanism 120 can include a first gear that is mechanically coupled to the bending feature 112, e.g., by a cable. The cable can be disposed in a channel that extends through the length of the elongated body 102 or can be embedded in solid material of the elongated body 102. In some examples, the extendible feature 110 and the bending feature 112 can be electronically controlled by the control mechanism 120. For instance, the control mechanism 120 can be electronically coupled by a wired or wireless connection to the bending feature 112 such that electronic signals from the control mechanism 120 controls operation of the bending feature 112.

One or more functionalities, such as suction or cautery, can be performed by components integrated into the device 100. In some examples, a cautery tool can be integrated into the tool channel 104 or a dedicated cautery channel. An interventionist can advance the cautery tool through the channel and out from the distal end 106 of the device to make use of the cautery function without having to insert a distinct cautery tool into the tool channel 104. In some examples, a suction tool can be integrated into the tool channel 104 such that an interventionist can advance the suction tool through the channel and out from the distal end 106 of the device to apply suction to the intervention site. In some examples, a dedicated suction channel through the body 102 of the device can terminate at one or more openings at the distal end 106 of the device and/or along the length of the body 102. A proximal end of the suction channel can be configured to connect to a suction source, such as a vacuum pump.

One or more inflatable or expandable structures, such as balloons, foam, soft actuators, or other inflatable or expandable structures can be disposed along the length of the elongated body 102. The inflatable or expandable structures can be integrated into the device 100 as fixed components or can be removable, e.g., allowing the device to be operated with or without the structures or allowable one type of structure to be exchanged for another. In the example of FIGS. 2A and 2B, a first balloon 140 is disposed at the distal tip 106 of the elongated body 102 and a second balloon 142 is disposed near the bending feature 112. The inflatable structures can be made of a flexible, biocompatible material.

The inflatable structures 140, 142 can be inflated with gas or liquid, such as saline. When inflated, the inflatable structures 140, 142 can serve to stabilize the device 100 at the intervention site. For instance, when used in a beating heart, the inflated structures 140, 142 can couple the device with the beating heart so that the heart does not beat into the field of view of the imaging system 120 and so that the beating heart does not move the device 100 out of position.

In some examples, the exterior surface of the inflatable structures 140, 142 is smooth relative to the exterior surface of the elongated body 102. For instance, a roughness of the inflatable structures 140, 142 can differ from a roughness of the elongated body 102. The roughness of the inflatable structures 140, 142 can be lower than or higher than the roughness of the elongated body 102. In some example, the roughness of the inflatable structures 140, 142 can be lower than the roughness of the elongated body 102 such that the inflatable structures 140, 142 are relatively smooth. The smooth exterior surface of the inflatable structures 140, 142 can help mitigate friction between the device 100 and tissue, e.g., enabling the device 100 to slide smoothly through an incision and into the heart.

In some examples, the exterior surface of the inflatable structures 140, 142 can include a textured surface. The exterior surface of the inflatable structures 140, 142 can be textured or covered with textured surface, e.g., corrugated or irregularly textured. A textured exterior surface can provide adhesion or traction between the device 100 and tissue, e.g., for stabilization of the device by increasing friction or grasping the heart or pericardial surface and by applying traction to the tissues to facilitate dissection, thus enabling safe manipulations.

One or more of the inflatable structures 140, 142 can be equipped with monitoring capabilities, such as electrocardiogram (EKG) monitoring or temperature monitoring. Monitoring capabilities integrated into the inflatable structures 140, 142 can provide insight into the local condition of the patient at or near the target site. For instance, EKG monitoring can provide continuous assessment of the patient's heart function as the inflatable structures 140, 142 are inflated to provide early warning of abnormalities. Temperature monitoring can provide an indication of whether tissue is being maintained at a safe temperature during an ablation procedure, such as cryoablation or radiofrequency ablation. In addition, the inflatable structures can provide protection for and act as a barrier to important structures like the phrenic nerve and esophagus during ablation process, which can reduce the risk of adverse effects of the procedure.

Although two inflatable structures 140, 142 are shown in FIG. 1, in some examples, more than two inflatable structures can be used. In some examples, a single, elongated inflatable structure can be disposed along some or all of the length of the elongated body 102. In some examples, the one or more inflatable structures can be attached to the elongated body 102 in a fixed position. In some examples, the positions of the one or more inflatable structures along the length of the elongated body 102 can be adjustable. The inflatable structures can be any of a variety of shapes, such as circular, toroidal, oval, quadrangular, or another shape that cover circumferentially or partially the elongated body 102. The inflatable structures include multiple sub-compartments. For example, the inflatable structures can include 2, 3 or 4 balloons attached to each other to form one inflatable structure, each of the balloons corresponding to a sub-compartment of the one inflatable structure.

In some examples, the exterior surface of the body 102 of the device can be coated with a low friction coating to help mitigate friction between the device 100 and tissue, e.g., enabling the device 100 to slide smoothly through an incision and into the heart.

A handle 150 at the proximal end 108 of the device provides a gripping region with which the interventionist can control the operation of the device. For instance, the control mechanism 120 can be provided on the handle 150. In some examples, the proximal end 108 of the device can be connected to a fixation mechanism, such as a stabilization arm, that can be rigidly affixed to a base, e.g., a surgical or procedure table, to hold the device 100 in place during the intervention procedure.

Optical Systems

The device 100 includes an optical system 130 for imaging the site of the intervention procedure. The optical system 130 includes a camera (e.g., a still camera or a video camera) and an illumination source, such as a light emitting diode (LED) or an optical fiber. The optical system 130 is disposed at or near the distal end 106 of the device and positioned such that the camera is able to acquire images of the site of the intervention procedure. For instance, the camera can be positioned to acquire images of a site up to about 3 mm in front of the distal end 106 of the device 100, and the illumination source can be positioned to provide substantially uniform illumination throughout the field of view of the camera.

The camera of the optical system 130 can be, for instance, a charge-coupled device (CCD) camera (e.g., a 5 mm diameter CCD camera) or a complementary metal-oxide semiconductor (CMOS) camera (e.g., a 1 mm×1 mm×1 mm CMOS video camera (250×250 pixels, Naneye, Awaiba, Inc., Funchal, Madeira, Portugal)). The camera can be a three-dimensional, four-dimensional, or 360-degree camera. In some examples, the position and/or the focus of the camera can be adjusted, e.g., by control electronics at the proximal end 108 of the device or by remote control. In some examples, the camera position and angle of view with respect to the axis of the device can be parallel to allow visualization of the device as it exits the transparent bulb while still providing a field of view of structures beyond the distal end of the transparent bulb, e.g., about 1 to 5 cm beyond the distal end of the transparent bulb. In some examples, the camera angle can be more than 0 degrees with respect to the device axis to increase visualization of the tip of the working channel. In some examples, the camera view can be rotated or angulated using geometric shapes (e.g., prism) which can be placed in front of the optical system 130 or in a field of view of the optical system 130.

The camera of the optical system 130 can be positioned inside the body of the device 100 or at the distal end 106 of the device. In some examples the camera can be connected to the proximal end 108 and the image can be transmitted from the camera at the distal end 106 to a control electronics using optic fibers or other modality of image transmission.

The illumination source can emit visible light (e.g., white light or light of a specific wavelength or range of wavelengths), infrared light, near-infrared light, and/or ultraviolet light. In some examples, the illumination source can be one or more LEDs disposed at the distal end 106 of the device 100. For instance, the illumination source can be a 1.6 mm×1.6 mm LED (Cree Inc., Durham, NC). In some examples, the illumination source can be an optical fiber that terminates at the distal end 106 of the device 100. The optical fiber can be embedded in the solid material of the body 102 or disposed in a channel extending through the length of the body.

The optical system 130 can be coupled through a wired electrical connection to a power source, control electronics, and/or data storage devices. In the case of a wired connection, the wires can be embedded in the solid material of the body 102 of the device 100. In some examples, the wires can be contained in a sealed, fluid-tight package that is threaded through a channel in the device 100, such as the tool channel 104 or a dedicated optical channel. In some examples, the optical system 130 can be configured for wireless power and/or data transmission.

A transparent bulb 160 is formed or attached at the distal end 106 of the device. The transparent bulb 160 acts as an enclosure that fluidically isolates the optical system 130 from the exterior of the device 100, e.g., from tissue and body fluids external to the device 100. Fluidically isolating the optical system 130 helps to prevent electrical signals from the imaging system 130 from being carried to the intervention site by tissue, blood, or the device, thus helping to avoid unintended electrical stimulation of the intervention site. The transparent bulb 160 can be formed of a biocompatible material that is transparent to the wavelength of the illumination source. For instance, the transparent bulb 160 can be formed of silicone, polycarbonate, polypropylene, polyacetal, polyetheretherketone (PEEK), acrylic, or other materials.

FIGS. 4A-4D depict various embodiments of a transparent bulb 400, 420, 440, 460, respectively. Each of the bulbs 400, 420, 440, 460 has a flat proximal surface 402, 422, 442, 462, respectively, thus enabling the transparent bulb to align closely with the distal end surface of the body 102 of the device. A distal surface 404, 424, 444, 464, respectively, of the transparent bulb can be any of a variety of shapes, such as rounded, flat, sloped, or another shape. Examples of shapes for the distal surface are shown in FIGS. 4A-4D. For instance, the shape of the distal surface of the transparent bulb can be selected based on the type of procedure to be performed with the device 100.

A working channel 406, 426, 446, 466 formed through the transparent bulb 400, 420, 440, 460 is aligned with the tool channel 104 in the body 102 such that a tool inserted through the tool channel 104 in the body 102 emerges through the opening of the working channel 406, 426, 446, 466 in the transparent bulb 400, 420, 440, 460 to access the intervention site.

A visualization channel 408, 428, 448 is positioned in the field of view of the optical system 130 (e.g., a camera) to provide a clear, unobstructed field of view through which the intervention site can be imaged. In some examples, the visualization channel 408, 428, 448 can cause internal reflection of the illumination from the optical system 130. To mitigate internal reflections by the visualization channel 408, 428, 448, the visualization channel 408, 428, 448 can be filled with a transparent fluid. The transparent fluid can have an index of refraction that allows for adjusting the refraction of light being emitted from the light source to the intervention site and back from the intervention site to the camera of the optical system. For instance, the transparent fluid can have an index of refraction substantially the same as the index of refraction of the transparent bulb 160 itself. In a specific example, the visualization channel 408, 428, 448 can be filled with glycerol. In some examples, internal reflections can be mitigated by providing an anti-reflective coating on the inner surface of the visualization channel 408, 428, 448. In some embodiments, the device does not include the visualization channel. In some examples, the transparent bulb 400, 420, 440 is formed such that the optical properties of the transparent bulb in the field of view of the optical system 130 are not susceptible to internal reflection from the illumination. In some examples, the bulb may not have a visualization channel in front of the optical system, as shown in the bulb 460 of FIG. 4D.

Figure 5:
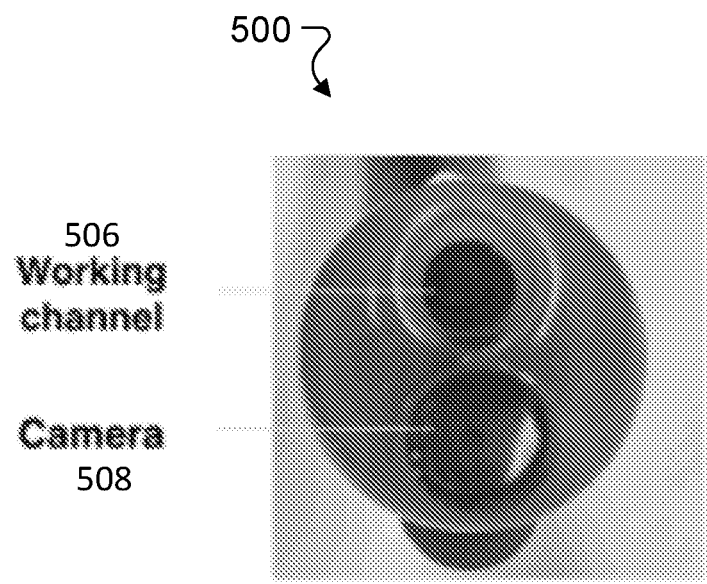
FIGS. 5 and 6 are photographs of the distal end of a transparent bulb of embodiments of an adjustable configuration device.

FIG. 5 is a photograph of the distal face of an example of a transparent bulb 500, showing a working channel 506 and a visualization channel 508.

Figure 6:
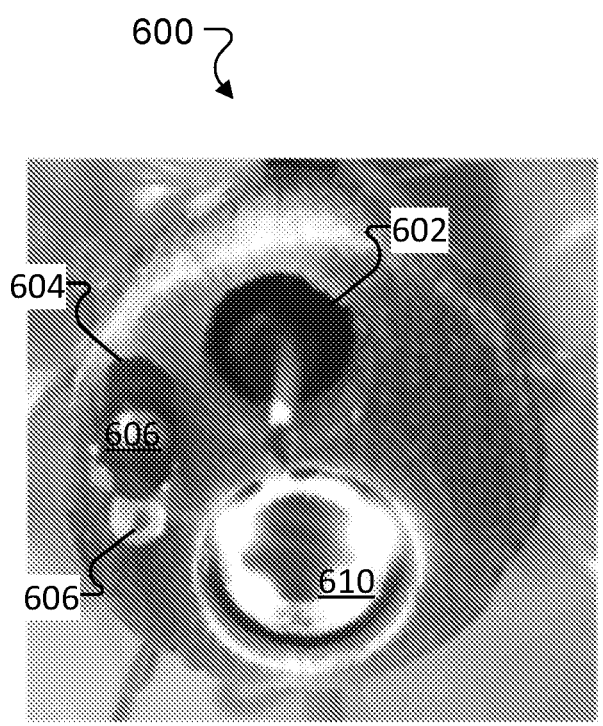

FIG. 6 is a photograph of the distal end of an example adjustable intrapericardial navigation device 600 having multiple channels. In particular, the adjustable intrapericardial navigation device 600 includes a working channel 602, such as a 5 mm channel, for receiving an instrument sized to fit in the working channel 602. The adjustable intrapericardial navigation device 600 includes a second working channel 604 for receiving an instrument. The working channel 604 can have the same diameter as the working channel 602 or can have a larger or smaller diameter. In the example of FIG. 6, the working channel 604 is for a diathermy instrument 606. In some examples, a diathermy instrument can be integrated into the body of the adjustable intrapericardial navigation device 600 rather than inserted through a channel. The adjustable intrapericardial navigation device 600 includes a suction channel 606. In some examples, a suction tube can be integrated into the body of the adjustable intrapericardial navigation device 600 rather than inserted through a channel. The adjustable intrapericardial navigation device includes an optical system 610 including a camera and an LED light aligned with a visualization channel.

Figure 7:
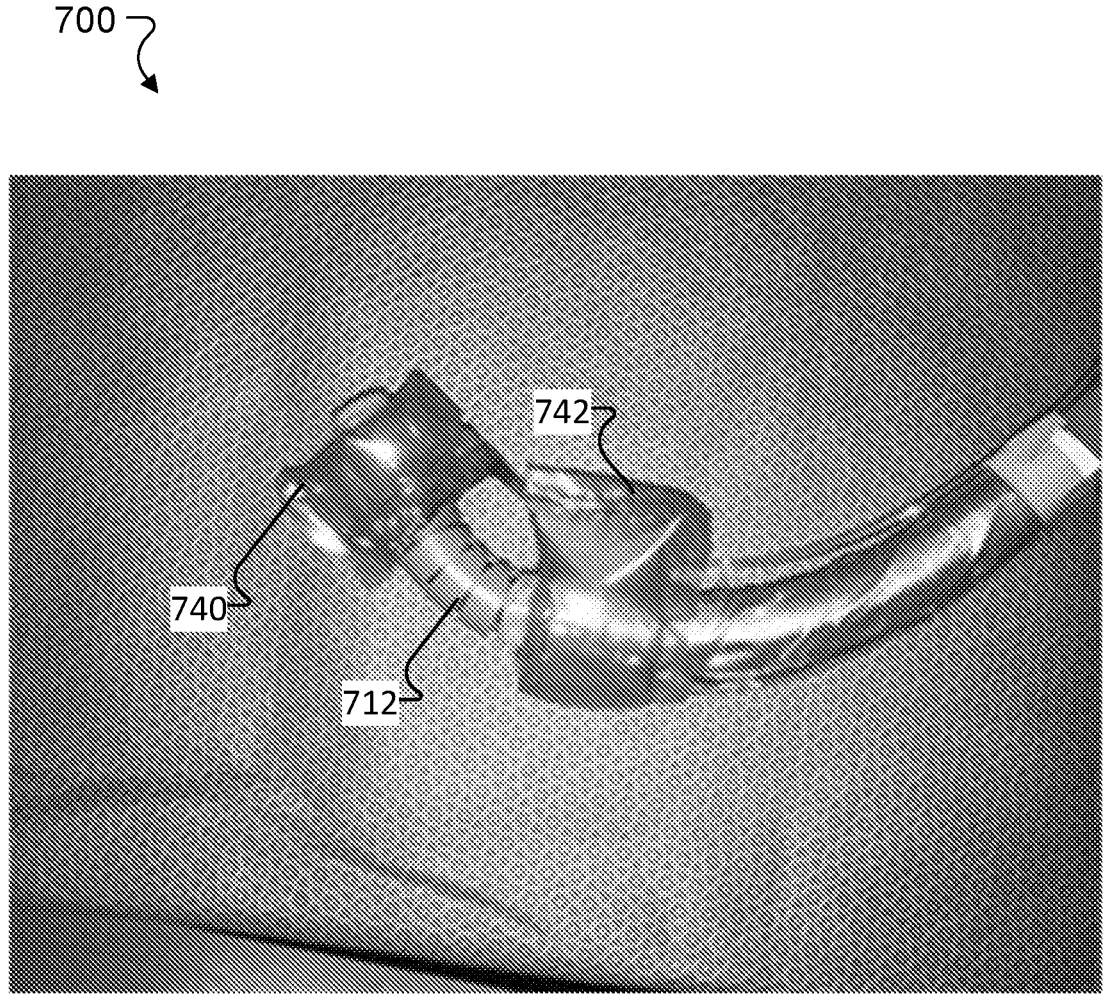
FIG. 7 is a photograph of an example of an adjustable configuration device.

FIG. 7 is a photograph of an example of the distal end of an adjustable intrapericardial navigation device 700. A first bending feature 712 at the distal end enables the angle of the distal tip of the adjustable intrapericardial navigation device 700 to be adjusted. Two inflatable balloons 740, 742 are disposed along the length of the adjustable intrapericardial navigation device to provide stability.

Figure 8A:
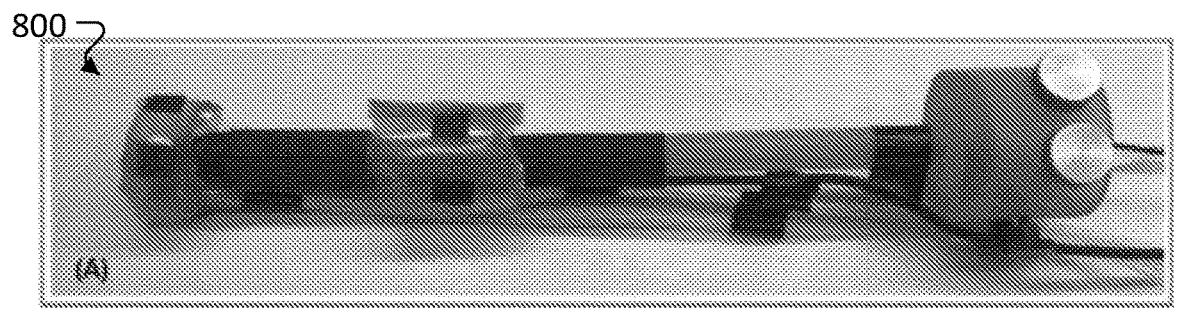
FIGS. 8A-8C are photographs of an example of an adjustable configuration device.
Figure 8B:
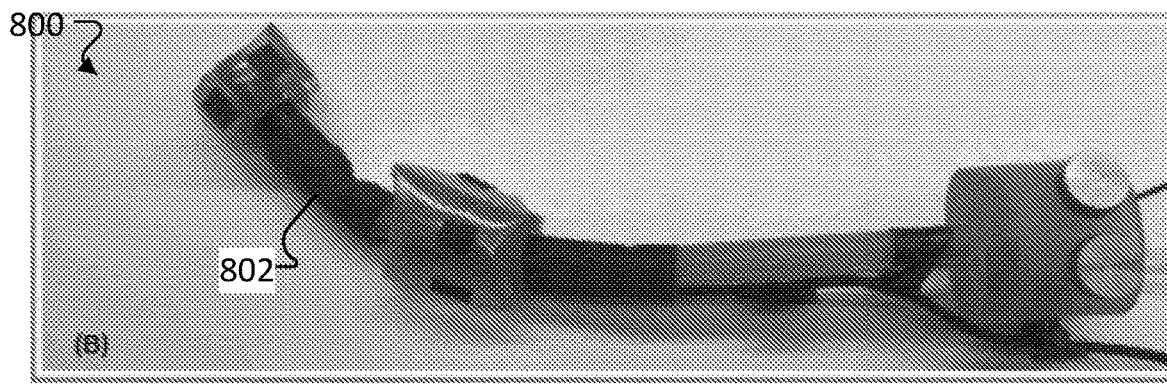
Figure 8C:
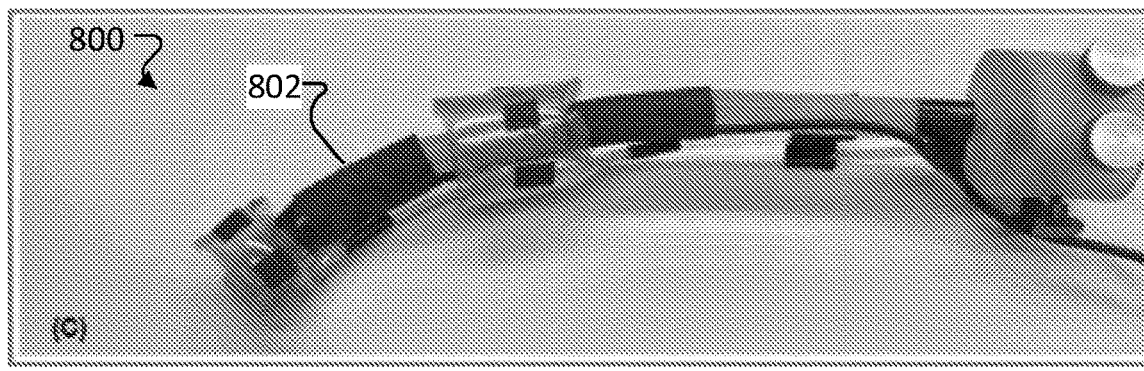
Figure 9A:
FIGS. 9A-9C are photographs of an example of an adjustable configuration device.
Figure 9B:
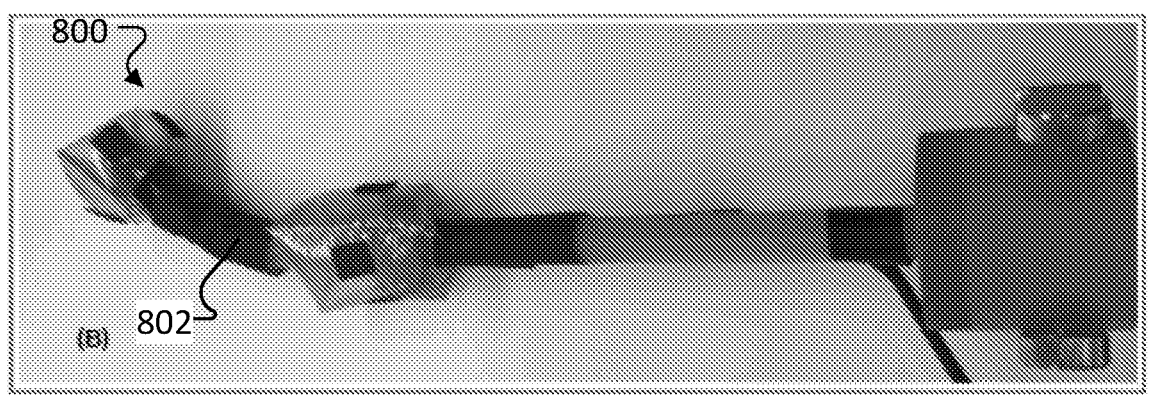
Figure 9C:
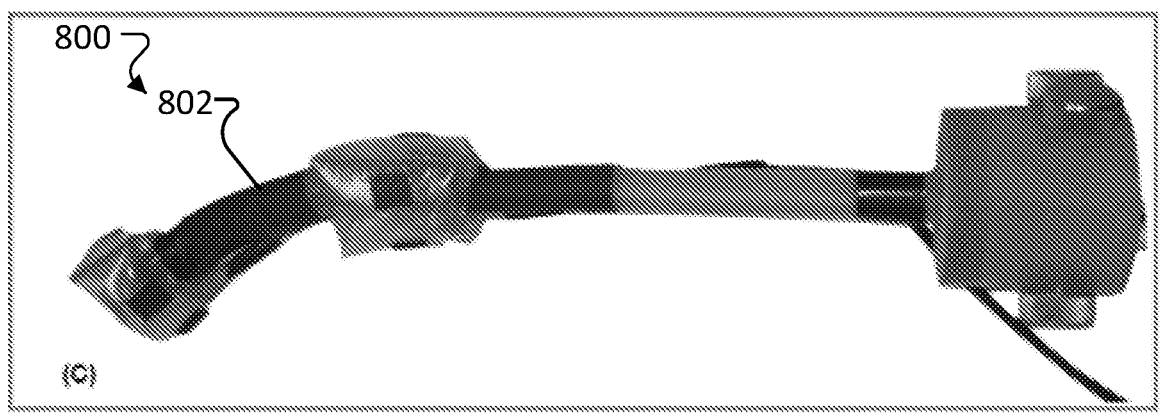

FIGS. 8A-8C are photographs of a side view of an example adjustable intrapericardial navigation device 800. FIGS. 9A-9C are photographs of a top view of the example adjustable intrapericardial navigation device 800. These figures depict the ability of the distal end of the device to pivot around a bending feature 802 at the distal end of the device. FIGS. 8A and 9A show the device 800 in a straight configuration, FIGS. 8B and 9B show the device 800 with the distal end pivoted upwards around the bending feature 802, and FIGS. 8C and 9C show the device 800 with the distal end pivoted downwards.

Figure 10A:
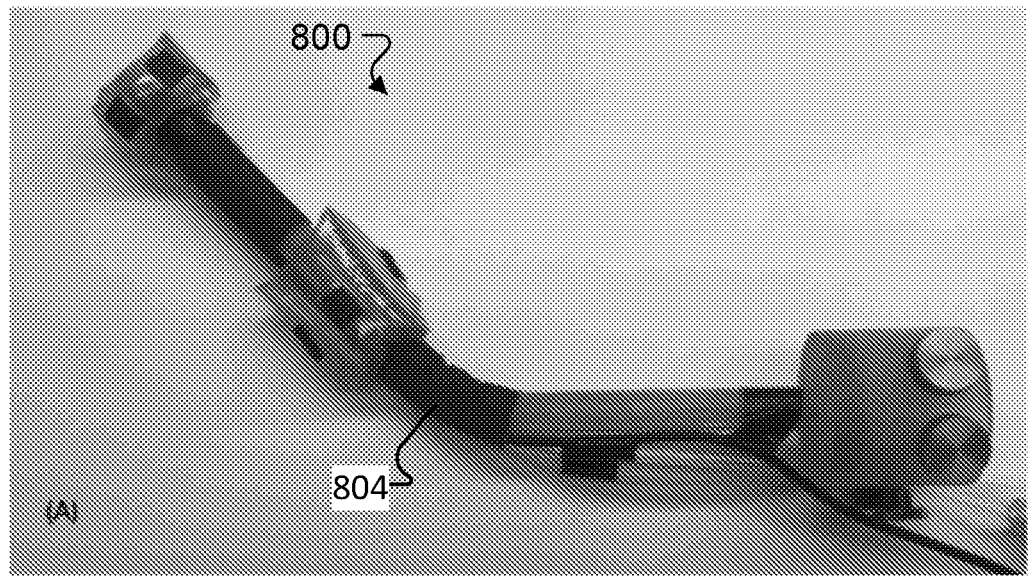
FIGS. 10A and 10B are photographs of an example of an adjustable configuration device.
Figure 10B:
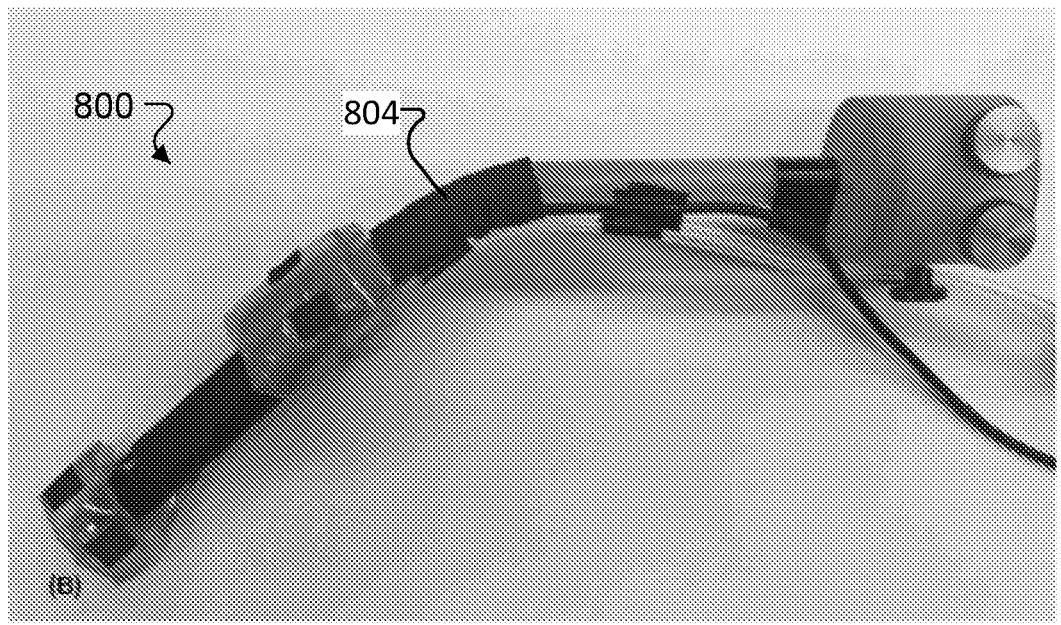

FIGS. 10A and 10B are photographs of a side view of the example adjustable intrapericardial navigation device 800 depicting the ability of the device to be bent around a bending feature 804 along the length of the device, e.g., towards the middle of the device. FIG. 10A shows the device 800 bent upwards at the bending feature 804 and FIG. 10B shows the device 800 bent downwards at the bending feature 804.

Figure 11:
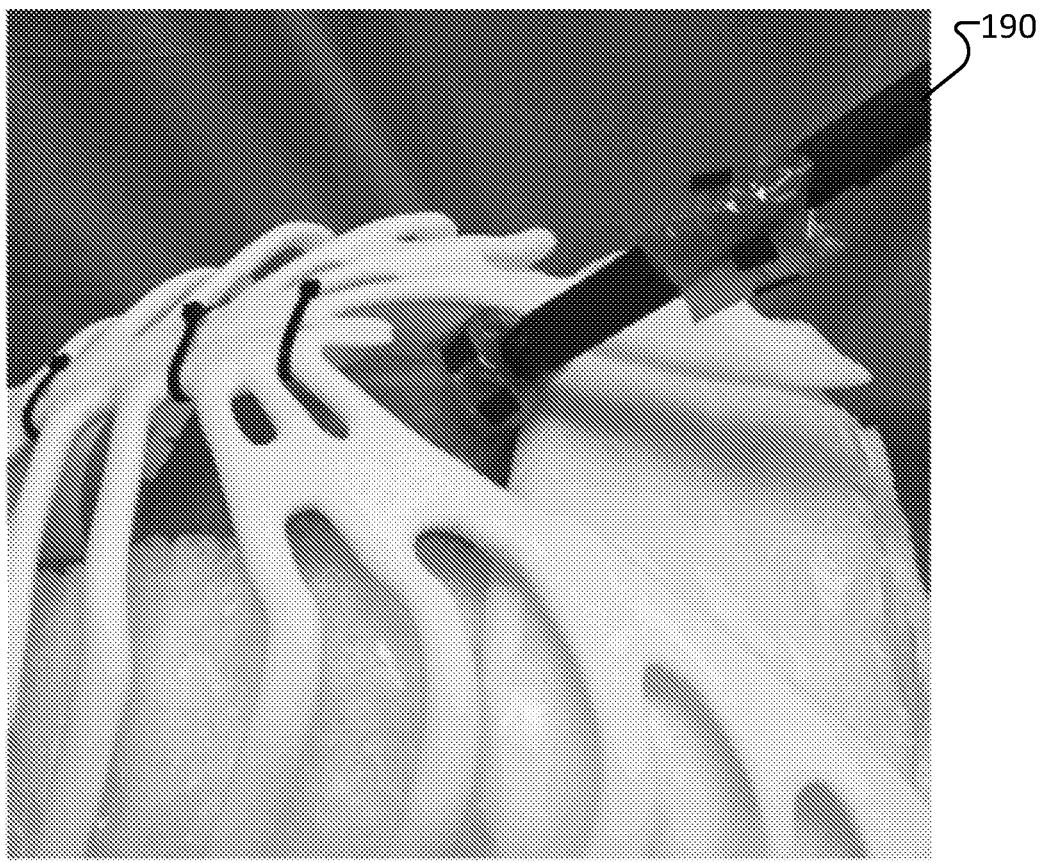
FIG. 11 is a photograph of an adjustable configuration device inserted into a body through the sub-xiphoid approach

FIG. 11 is a photograph of an adjustable intrapericardial device 190 inserted into a body through the sub-xiphoid approach.

Use of the Device for Cardiac Ablation

Figure 12:
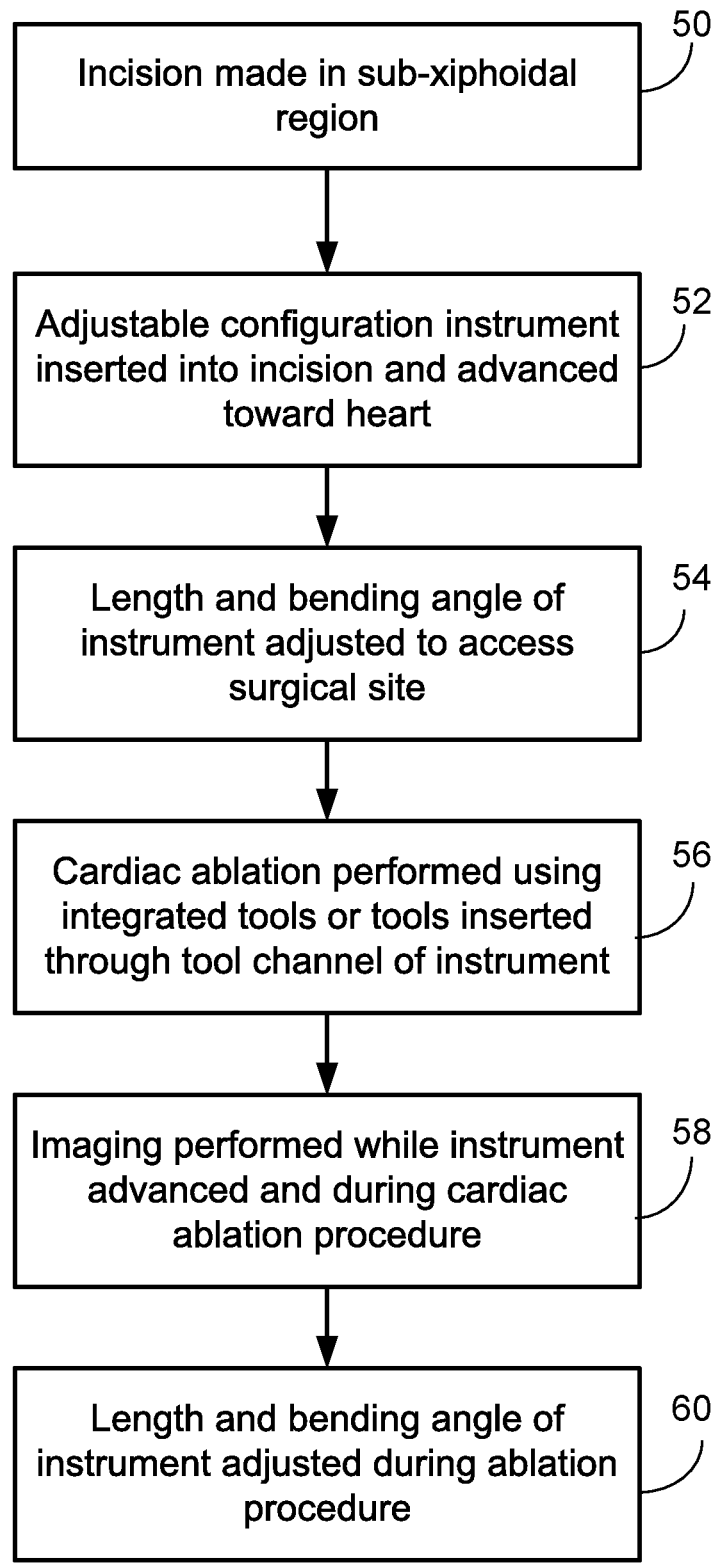
FIG. 12 is a flow chart of steps in a procedure carried out using an adjustable configuration device as described herein.

FIG. 12 provides a flow chart of an example of a cardiac ablation procedure using the new devices described herein. First, an incision is made in the patient's subxiphoidal region (50). An adjustable configuration device is inserted into the incision and advanced toward the patient's heart (52), e.g., passing directly through the pericardium to access any target area on the external surface of the heart or bilateral heart structures. By approaching the heart through a single, subxiphoidal incision, other organs, such as abdominal organs (e.g., liver) and lungs, can be avoided. Furthermore, both ventricles and atria of the patient can be accessed without exerting significant pressure on the patient's heart.

The length and bending angle of the device are adjusted as appropriate to access the intervention site in the patient's heart (54). For instance, the device may be elongated for a patient having a larger-than-average distance between the subxiphoidal region and the target on the heart. The device may be bent to an angle that enables the surgical or intervention site to be accessed from the subxiphoidal incision while avoiding other internal organs.

In some examples, a textured surface of the inflatable structure is inflated to provide stability for the device and hence the visual field of an imaging system of the device. The inflation of the inflatable structure can also provide a barrier to surrounding organ structures.

Interventional tools inserted through the tool channel can also be used to perform the cardiac ablation procedure once the device is positioned at the intervention site (56). In some examples, one or more tools that are integrated into the device can also be used to access the intervention site or to perform the cardiac ablation procedure. Imaging can be performed while the device is advanced toward the intervention site and while the cardiac ablation procedure is performed (58). During the procedure, the length and/or bending angle of the device can be adjusted as appropriate (60), e.g., to perform ablation in a straight, continuous region of tissue.

Alternative Embodiments

Figure 13:
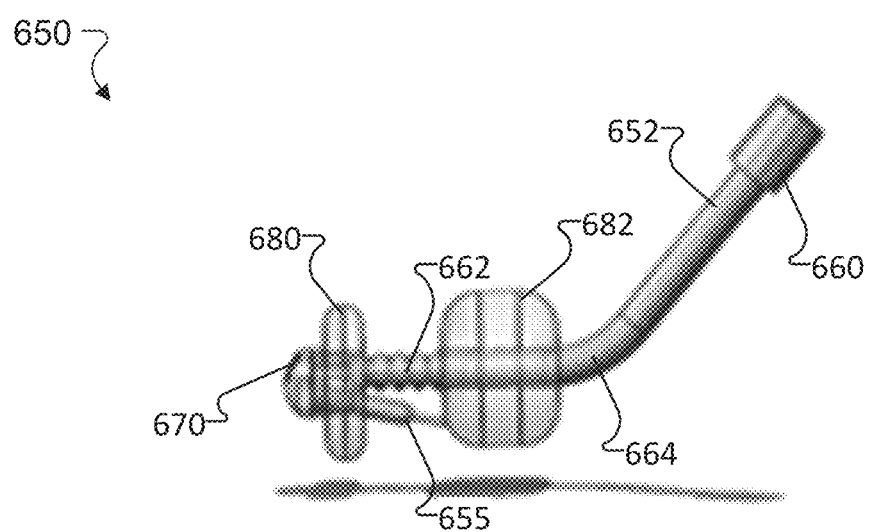
FIG. 13 is a diagram of an alternative embodiment of an adjustable configuration device.

FIG. 13 shows an alternative embodiment of an adjustable configuration device 650 that includes a body 652 with a first bending feature 662, a second bending feature 664, and an extendible feature 660. A transparent bulb 670 is formed at the distal end of the device 650. Two inflatable structures 680, 682 are disposed along the length of the body 652. One or more components 655 of the device 650, such as an optical system, integrated cautery, or integrated suction, are positioned adjacent the body 652, with the distal end of the components 655 terminating at the distal end of the transparent bulb 670.

In certain examples described herein, the adjustable configuration devices are used for minimally invasive surgical procedures such as cardiac ablation. In some examples, the adjustable configuration devices described here can be used for other types of minimally invasive surgical procedures in which variations in patient anatomy may call for devices of various lengths or angular configurations or in which the surgical procedure involves small-scale, fine movement of the device. For instance, the devices described here can be used or modified (e.g., straight device, fixed angle device, or device with one adjustable site in the middle or near by the tip) for surgical procedures such as pericardium exploration, left atrial appendage closure device delivery, adhesion removal, mediastinal mass and lymph node biopsies, patent ductus arteriosus closure, or other minimally invasive procedures, such as abdominal procedures or intrauterine fetal scope procedures. Intrapericardial navigation devices are described herein. In other examples, the devices are intervention devices that can be used for applications other than intrapericardial navigation, e.g., other organ interventions, surgical interventions, or other interventions.

In certain examples described herein, the imaging system is described as being disposed at a distal end of an intervention device. In other examples, the imaging system is disposed a proximal end of an intervention device. In further examples described herein, the length-adjustable element is disposed a proximal end of an intervention device. In other examples, the length-adjustable element is disposed at a distal end of an intervention device. The imaging system and the length-adjustable element can be disposed on the same end of the intervention device.

Other Embodiments

A number of embodiments of the invention have been described. Nevertheless, it will be understood that various modifications can be made without departing from the spirit and scope of the invention. For example, some of the steps described above may be order independent, and thus can be performed in an order different from that described.

Other implementations are also within the scope of the following claims.

What is claimed is:

1. A method for performing cardiac ablation a surgical procedure at a target site in a patient, the method comprising:
   inserting a device into a subxiphoidal incision in the patient, wherein the device comprises an elongated body including a tool channel extending therethrough from a proximal end to a distal end of the elongated body;
   adjusting a length of the elongated body using a length-adjusting element disposed at the proximal end of the elongated body, and adjusting an angle between portions of the elongated body by adjusting an angle of an angle-adjusting element disposed between the proximal end and the distal end of the elongated body at a more distal position than the length-adjusting element,
   wherein the adjustment of the length of the elongated body and the adjustment of the angle of the elongated body bend the elongated body around tissue to position the distal end of the elongated body at a target site on a heart of the patient from the subxiphoidal incision;
   inflating first and second inflatable structures of the elongated body, where the first inflatable structure is intermediate between the proximal end and the distal end of the elongated body, and wherein the second inflatable structure is at the distal end of the elongated body, the second inflatable structure spaced apart from the first inflatable structure,
      wherein inflation of the first inflatable structure couples the device with the heart while the heart beats, such that the device retains its position with respect to the heart while the heart beats;
   inserting an intervention tool through the tool channel of the elongated body to the distal end of the elongated body;
   ablating the target site using the intervention tool while the device is coupled with the heart by the first inflatable structure; and
   obtaining an image of the target site, the intervention tool, or both using an imaging system disposed at the distal end of the elongated body while the device is coupled with the heart by the first inflatable structure.

2. The method of claim 1, wherein the device comprises, at a distal end of the elongated body, a cutout that allows the device to bend in response to pressure.

3. The method of claim 1, wherein the imaging system comprises one or more of a camera or an optical fiber.

4. The method of claim 1, wherein the first inflatable structure and the second inflatable structure have a surface roughness that is smoother than a surface roughness of an outer surface of the elongated body.

5. The method of claim 1, wherein the device comprises a monitoring device integrated into the first inflatable structure or the second inflatable structure, wherein the monitoring device comprises one or more of an electrocardiogram (EKG), a temperature sensor, or an infrared sensor.

6. The method of claim 1, wherein the first inflatable structure and the second inflatable structure are compartmentalized into multiple inflatable sub-compartments that are attached to one another to form the first inflatable structure and the second inflatable structure.

7. The method of claim 1, wherein the device comprises a suction system configured to apply a suction at one or more of the distal end or a side of the elongated body.

8. The method of claim 1, wherein the device comprises a cautery mechanism disposed at the distal end of the elongated body.

9. The method of claim 1, wherein adjusting the length is performed using a control mechanism mechanically connected to the length-adjusting element.

10. The method of claim 9, wherein the control mechanism comprises a first gear for controlling the length-adjusting element.

11. The method of claim 1, wherein ablating the target site is performed while the heart beats.

12. The method of claim 1, wherein the length-adjusting element comprises a telescopic element at the proximal end of the elongated body.

13. The method of claim 1, wherein the angle-adjusting element comprises a hinge, an accordion feature, or a ball-and-socket joint.

14. The method of claim 1, wherein inflating the first and second inflatable structures comprises filling the first and second inflatable structures with fluid.

15. The method of claim 1, further comprising monitoring one or more of an electrocardiogram (EKG), a temperature, or tissue characteristics at the target site.

16. The method of claim 1, comprising adjusting an angle of the distal end of the elongated body using another angle-adjusting element immediately adjacent to the imaging system.

17. The method of claim 1, wherein the angle-adjusting element is configured to enable the elongated body to be bent to an angle up to 140°.

* * * * *

UNITED STATES PATENT AND TRADEMARK OFFICE
CERTIFICATE OF CORRECTION

PATENT NO. : 12,251,525 B2  
APPLICATION NO. : 16/762076  
DATED : March 18, 2025  
INVENTOR(S) : Mossab Y. Saeed et al.

Page 1 of 1

It is certified that error appears in the above-identified patent and that said Letters Patent is hereby corrected as shown below:

In the Claims

Column 12, Lines 30-31, Claim 1, after "ablation" delete "a surgical procedure at a target site".

Signed and Sealed this
Sixth Day of May, 2025

Coke Morgan Stewart
*Acting Director of the United States Patent and Trademark Office*